United States Patent [19]

Levitt

[11] 4,443,761

[45] Apr. 17, 1984

[54] NMR SPECTROSCOPY

[75] Inventor: Malcolm H. Levitt, Hull, England

[73] Assignee: National Research Development Corporation, London, England

[21] Appl. No.: 382,648

[22] Filed: May 27, 1982

[30] Foreign Application Priority Data

Jun. 16, 1981 [GB] United Kingdom ............... 8119000

[51] Int. Cl.³ ............................................. G01R 33/08
[52] U.S. Cl. .................................... 324/311; 324/314
[58] Field of Search ............... 324/300, 307, 308, 311, 324/313, 314

[56] References Cited

U.S. PATENT DOCUMENTS

| | | | |
|---|---|---|---|
| 3,474,329 | 10/1969 | Waugh | 324/311 |
| 3,530,374 | 9/1970 | Haeberlen et al. | 324/311 |
| 3,781,650 | 12/1973 | Keller | 324/311 |
| 3,787,760 | 1/1974 | Keller et al. | 324/311 |
| 4,068,161 | 1/1978 | Ernst | 324/311 |

Primary Examiner—Michael J. Tokar
Attorney, Agent, or Firm—Cushman, Darby & Cushman

[57] ABSTRACT

In a method of heteronuclear decoupling in high resolution pulsed NMR spectroscopy, during acquisition of signals emanating from a nuclear species to be observed (e.g. carbon-13), irradiation of an interfering nuclear species (e.g. protons) is effected by means of a train of composite pulses, each of which approximately inverts the longitudinal magnetisation, in the form of a repeated sequence comprising pairs of composite pulses of two types respectively having opposite r.f. phases.

6 Claims, 9 Drawing Figures

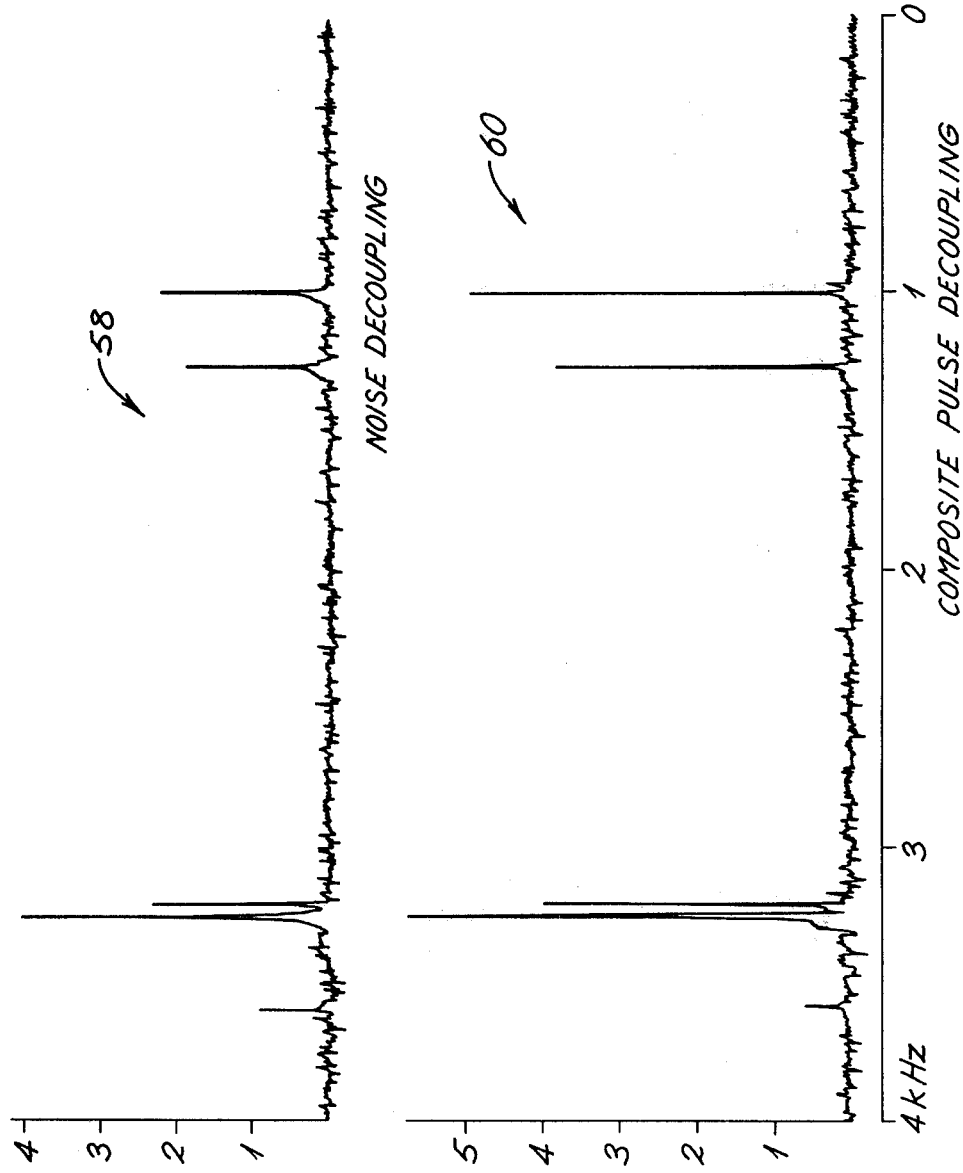

NMR SPECTROSCOPY

This invention relates to methods of heteronuclear decoupling in high resolution pulsed nuclear magnetic resonance (NMR) spectroscopy.

A NMR spectrum is subject to splitting of the desired nuclear signals into multiplets as a result of coupling between the spins of the nuclear species to be observed and those of other nuclei present in the sample under observation. Such heteronuclear coupling is characteristic of the grouping of nuclei in a molecule and is independent of static external conditions. In particular, coupling is independent of the strength of the static magnetic field used in the NMR technique, and the effect for a specific pair of nuclear species can be represented by a constant J. In simple cases the constant J defines the spacing between any two adjacent lines of the resultant multiplet and is therefore measured in units of frequency.

It is particularly important for a nuclear species of low natural abundance such as $^{13}C$ to obtain the maximum sensitivity and resolution of each chemically shifted line and clearly the creation of broad multiplets as a result of coupling reduces the line signal and makes the line position uncertain. The prevention or reduction of this interaction is known as decoupling and involves the application, during the acquisition from a sample of signals resulting from resonance of the nuclear species to be observed, of a perturbing field having a frequency in the region of resonance of the interfering nuclei. Commonly these nuclei are protons. In order to cover the range of proton resonance frequencies which are present in any specific chemical system it is usual to apply modulation in some form and a number of schemes have been proposed. The effect of the perturbing field may be regarded as the production of rapid transition between the spin levels of the proton. The lifetime of each spin state is then short compared with the time 1/J and ideally no net coupling effect is observed. It should be noted that this condition is much more stringent than that required for saturation of the spin system, in which transitions need only be induced at a rate which is fast compared with the inverse of the relaxation times.

In practice no general and valid theory of wideband decoupling has been available and the idealised conditions have been only partially satisfied. For example it is believed that in a pulse modulation scheme designed to cover the target proton frequency range, an implicit dependence on proportionality between the degree of decoupling at a particular frequency and the value of the Fourier component at that frequency cannot be justified. Consequently conventional procedures which result in a considerable degree of decoupling can leave uncompensated residual interactions sufficient to broaden the $^{13}C$ lines significantly and so reduce resolution and sensitivity.

It is an object of the invention to provide a procedure in which such residual interactions are substantially reduced.

According to the invention there is provided a method of heteronuclear decoupling in high resolution pulsed NMR spectroscopy in which, during the acquisition from a sample of signals resulting from resonance of a nuclear species to be observed, the sample is irradiated with radio frequency energy substantially at the resonant frequency of an interfering nuclear species, the irradiation being in form of a train of composite pulses each of which is effective to cause at least approximate inversion of the longitudinal magnetisation in respect of the interfering nuclear species, the composite pulses being of two types which differ only by virtue of the r.f. phase for one type being opposite that for the other type and the train being in the form of a repeated sequence which consists of two pulses of each type and which involves less than three changes of type between successive pulses.

If desired, the train of composite pulses may also be applied during the period immediately prior to the excitation of resonance of the nuclear species to be observed, in order to establish a wideband Overhauser enhancement.

The term 'composite pulse' is used herein in the the same sense as in the paper by Freeman et al published in J. Magn. Reson. Vol. 38, page 453 (1980), and refers to a pulse sequence (which may include at least one period of free precession between individual pulses) whose constituent pulses are associated in the sense that the state of the relevant nuclear spins is of interest only when the sequence has been completed. It should be noted that the reference to a train of such pulses is not intended to imply that there is necessarily an interval between successive composite pulses; indeed for the purposes of methods according to the invention it will normally be desirable for there to be no significant delay between successive composite pulses of the train. The term 'longitudinal' refers to the direction of the static magnetic field used in the NMR technique, about which the unperturbed spins of the interfering nuclear species precess.

One form of composite pulse suitable for use in a method according to the invention consists of three constituent pulses with negligible intervals between them, the first and third pulses having the same r.f. phase and each being of nominal duration $\pi/2\gamma B_2$, and the second pulse having a r.f. phase which differs by 90° from that of the first and third pulses and having a nominal duration between $\pi/\gamma B_2$ and $3\pi/2\gamma B_2$, where $B_2$ is the magnetic flux density associated with the r.f. irradiation and $\gamma$ is the gyromagnetic ratio for the interfering nuclear species; in conventional notation this form of composite pulse may be denoted by $90°(X)\alpha(Y)90°(X)$, where $\alpha$ has a value between 180° and 270° and X and Y refer to orthogonal directions perpendicular to the direction of the static magnetic field (in a reference frame rotating about the last-mentioned direction). This form of composite pulse is effective to achieve population inversion of the interfering nuclear spins in a manner which is relatively insensitive to resonance frequency offsets as compared with the use of a simple 180° pulse. The length of the second pulse (given by the angle $\alpha$) may be chosen according to the desired bandwidth of inversion relative to the irradiating field strength, which is conveniently expressed in units of frequency in accordance with the quantity $\gamma B_2/2\pi$. Thus where $\alpha$ has a value of 180° the relative effective bandwidth is about $2(\gamma B_2/2\pi)$, whereas it is only about half of this where $\alpha$ has a value of 240°; over this narrower offset range, however, the inversion is more accurate than in the case where $\alpha$ has the lower value.

An alternative form of composite pulse which may be used consists of two constituent pulses having the same r.f. phase and each of nominal duration $3\pi/2\gamma B_2$, separated by an interim period of duration approximately $2/\gamma B_2$ during which free precession may occur.

As noted above, in method according to the invention use is made of two types of composite pulse which differ only by virtue of the r.f. phase for one type being opposite that for the other type. Conveniently the two types of composite pulse may be denoted respectively by R and $\bar{R}$; for example if R has the form $90°(X)\alpha(Y)90°(X)$ then $\bar{R}$ will have the form $90°(-X)\alpha(-Y) 90°(-X)$. The specific forms of repeated sequence which may be used in a method according to the invention may then be denoted $RR\bar{R}\bar{R}$, $R\bar{R}\bar{R}R$, $\bar{R}RR\bar{R}$ and $\bar{R}R\bar{R}R$; these four sequences are equivalent in effect, as will be evident when it is noted that the four types of train respectively formed by repeating them differ only at the beginning and end of the train.

The invention will be further discussed, and examples of how it may be performed will be described, with reference to the accompanying drawings, in which:-

Figure 4:
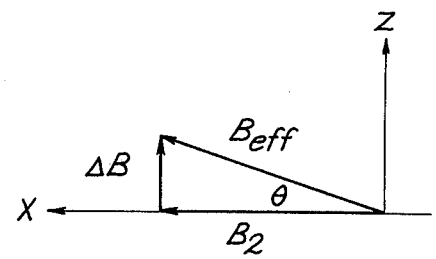
Figure 5:
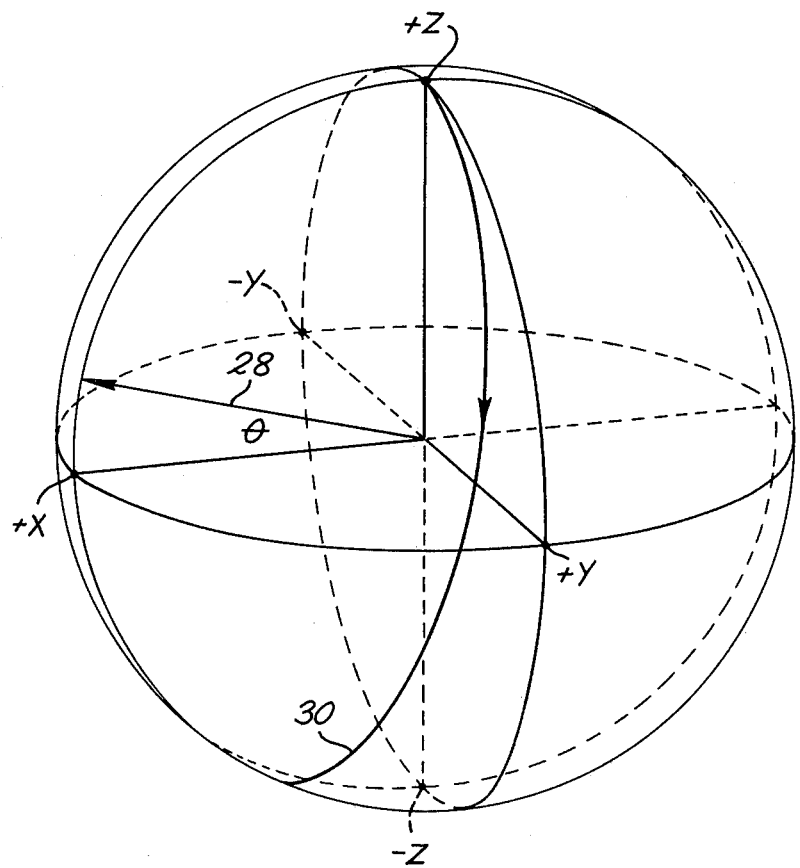
Figure 6:
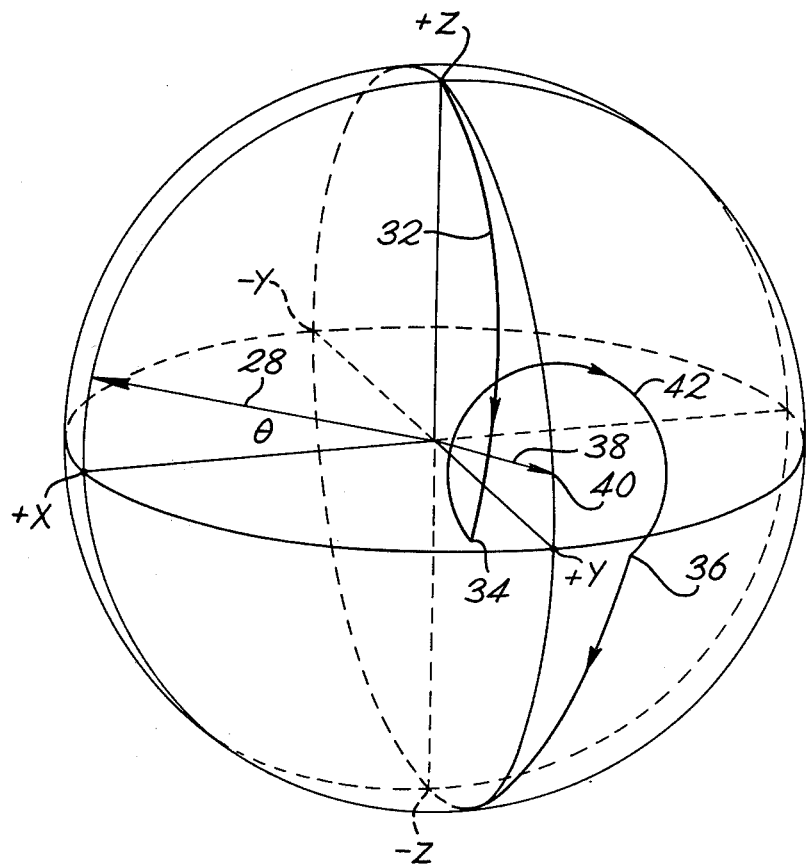
Figure 7:
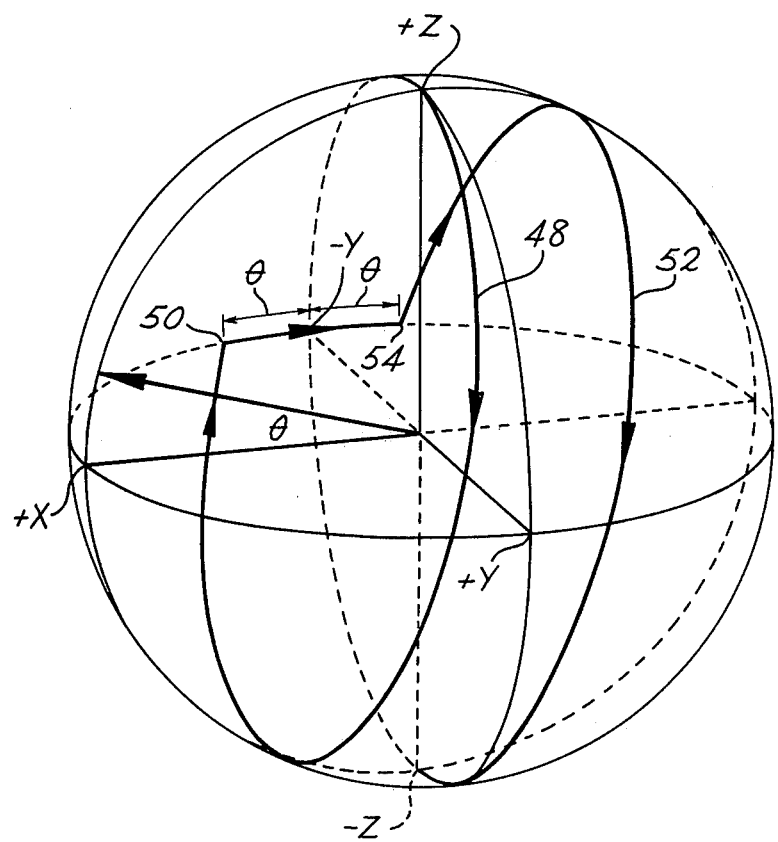
Figure 8:
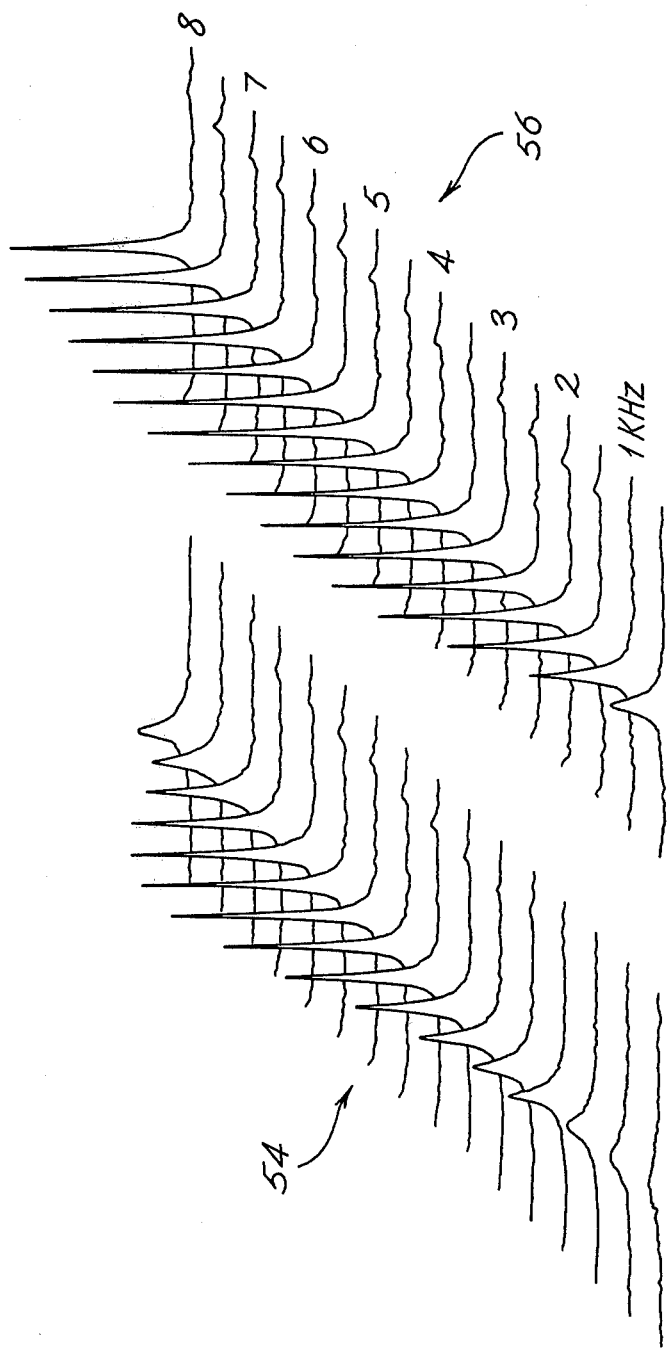

FIG. 4 indicates the independence of the effective decoupling field on resonance offset;

FIG. 5 represents in a rotating frame a longitudinal inversion trajectory produced by a single 180° pulse;

FIGS. 6 and 7 represent in a rotating frame the longitudinal inversion trajectories produced by alternative forms of composite pulse;

FIG. 8 shows comparative $^{13}C$ spectra for a range of resonance offset for a sample of methyl iodide subjected to noise decoupling and to composite pulse sequence decoupling in accordance with the invention: and FIG. 9 shows comparative $^{13}C$ spectra for a sample of ethyl benzene subjected to noise decoupling and to composite pulse sequence decoupling.

In the following description it is assumed for the sake of definiteness that the nuclear species to be observed is carbon-13, with protons constituting the interfering nuclear species.

Figure 1:
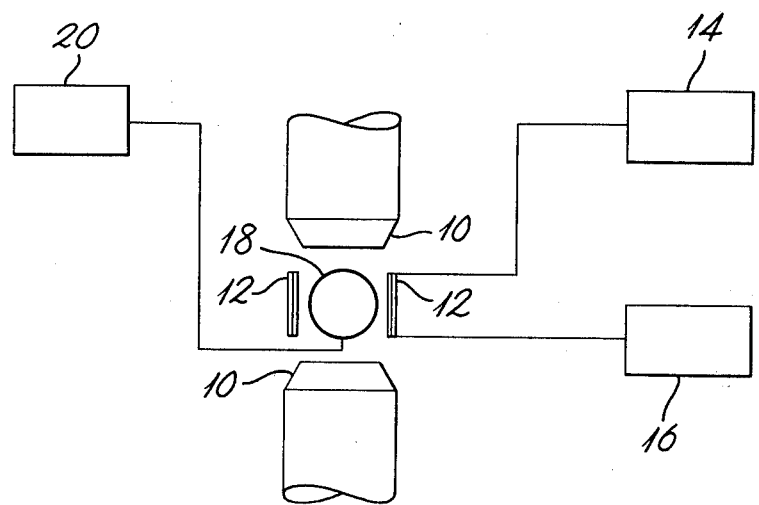
FIG. 1 is a diagrammatic representation of a spectrometer which may be used in practising the invention.

Referring to FIG. 1, a sample (not shown) containing these species is placed in a region of substantially uniform magnetic field $B_o$ which is produced between a pair of pole pieces 10. A pair of coils 12 arranged on an axis perpendicular to the direction of field $B_o$ receives r.f. pulses from a transmitter 14 to produce the required field $B_1$ for excitation of $^{13}C$ resonance. The transmitter 14 contains gating and delay elements for the control of duration and relative phase of the r.f. pulses. The coils 12 also serve to pick up the free induction decay signals from the sample, these signals being fed to a receiver 16 in which they are coherently detected, the detected signals being sampled to provide data from which the $^{13}C$ spectrum can be derived by conventional Fourier transformation. A further coil 18, which is shown for convenience as having an axis perpendicular to both $B_o$ and $B_1$, is used to produce a proton decoupling field $B_2$. The coil 18 is energised by a transmitter 20 having similar control facilities to those of the transmitter 14. For a field $B_o$ of about 2.1 tesla the proton decoupling transmitter frequency occupies a band near 90 MHz while the $^{13}C$ excitation frequency of the transmitter 14 is near 23 MHz. The required decoupling bandwidth depends on the chemical shifts which are present in the sample material and on the strength of field $B_o$, but typically a bandwidth of two kHz will be appropriate when $B_o$ has the value quoted above.

The transmitter 20 generates a continuous wave signal whose phase is changed at intervals (between levels of relative phase 0°, 90°, 180° and 270°) in a repetitive pattern such that the output of the transmitter 20 constitutes a train of composite pulses with negligible intervals between them. The composite pulses are of two types R and $\bar{R}$, respectively having the nominal forms $90°(X)$ $240°(Y)$ $90°(X)$ and $90°(-X)$ $240°(-Y)$ $90°(-X)$, and the repetitive pattern of phase changes is chosen so as to correspond to the sequence $RR\bar{R}\bar{R}$. It would of course be possible, with equivalent effect, to use instead one of sequences $R\bar{R}\bar{R}R$, $\bar{R}RR\bar{R}$, and $\bar{R}R\bar{R}R$. It will be appreciated that the actual duration of each composite pulse (and hence the repetition period for the sequence) will vary inversely in accordance with the value chosen for the strength of the decoupling field $B_2$. Where this value corresponds to about six kHz when expressed in units of frequency the duration of a composite pulse of the form $90°(X) 240°(Y) 90°(X)$ will be about 0.2 millisecond, so that the repetition period for the sequence will be about 0.8 millisecond.

The transmitter 20 is of course switched on throughout the period during which data are being acquired from the signals resulting from the $^{13}C$ resonance excited by a pulse from the transmitter 14. As a further contribution to sensitivity, the transmitter 20 may also be switched on during the period immediately prior to this pulse to provide nuclear Overhauser enhancement.

Figure 2:
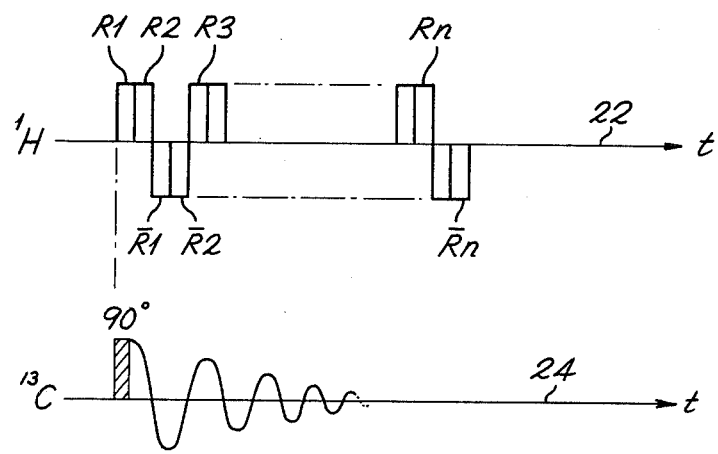
FIG. 2 represents diagrammatically a decoupling and acquisition pulse sequence for the spectrometer of FIG. 1.

FIG. 2 illustrates the arrangement in the case where the transmitter 14 is switched on to apply a $90°{}^{13}C$ acquisition pulse (as indicated on the lower axis 24) at the same time as the transmitter 20 is switched on to initiate the train of composite pulses (as indicated on the upper axis 22). For the purposes of illustration only, the two types of composite pulse R and $\bar{R}$ are respectively shown above and below the axis 22, with the pulses of each type serially numbered; the initial sequence constituted by the pulses R1, R2, $\bar{R}1$ and $\bar{R}2$ is of course identical with the sequence constituted by the pulses R3, R4, $\bar{R}3$ and $\bar{R}4$, and so on. The free induction decay signals are indicated by the oscillatory line following the $90°{}^{13}C$ pulse.

Figure 3:
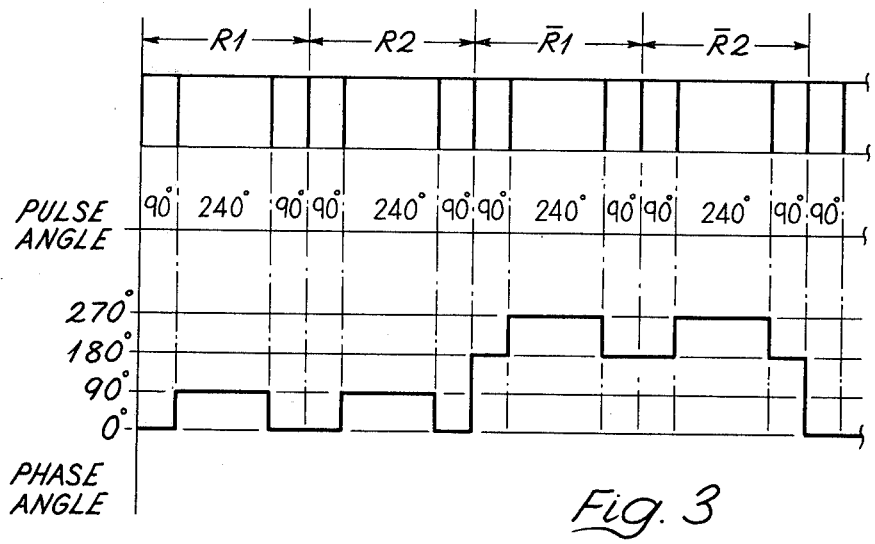
FIG. 3 represents diagrammatically the composite structure of the decoupling pulses of FIG. 2.

The structure and production of the train of composite pulses is illustrated in FIG. 3 with reference to the repetitive pattern of phase changes of the continuous wave signal generated by the transmitter 20, the phase angles of 90° and 240° of course referring to the constituent pulses which make up the composite pulses.

The experiment described above presents two distinct aspects for discussion. First, the constitution of the composite pulses such that sufficiently precise inversion of the proton magnetisation axis is produced and, second, the pulse sequence which reduces the residual coupling to a low level. The first requirement arises from the inherent defects of a nominally 180° pulse in any practical system. Exact inversion by means of a single 180° pulse becomes impossible for a proton at a particular site when the decoupling frequency is significantly offset from resonance. Such resonance offset, which is a most important problem in decoupling, is equivalent to introducing an additional component of field along the Z axis (i.e. parallel to field $B_o$). The relevant effective field then becomes appreciably stronger than $B_2$ and is directed at an angle to the transverse plane.

The effect of resonance offset is indicated in FIG. 4 which shows the XZ plane of a three axis reference frame, considered to be rotating about the Z axis in synchronism with the frequency of the decoupling transmitter. The $B_2$ field vector is represented along the X axis and the extent of resonance offset is represented by a component of field $\Delta B$ in the $+Z$ direction. The effective field $B_{eff}$, equal to $(\Delta B^2 + B_2^2)^{1/2}$ is tilted by an angle $\theta$ with respect to the X axis where $\theta = \tan^{-1} \Delta B/B_2$. Clearly a similar tilt would be observed with respect to the Y axis if the phase of field $B_2$ were shifted through 90°. The consequence is that during a $B_2$ pulse the proton magnetisation vector rotates about the axis of $B_{eff}$ instead of about the axis X (or Y). Referring now to FIG. 5, field $B_{eff}$ is represented as inclined on an axis 28 at angle $\theta$ to the X axis. It is apparent that a path 30 representing the trajectory of a vector rotated about axis 28 by a single 180° (X) pulse (which in the absence of defects would produce perfect inversion) will deviate progressively further from an initially followed line of longitude and from the $-Z$ pole.

The possibility of inversion error correction by means of a composite pulse can be visualised with reference to FIG. 6 in which a path 32 corresponds to the first part of path 30, reproduced from FIG. 5. If a 90°(X) pulse is applied by calculation from $B_2$, the rotation of the vector in the field $B_{eff}$ must be greater than 90°, since rotation varies inversely with the field value. Path 32 may therefore be expected to terminate at a point below the XY plane. However, because rotation occurs about the tilted $B_{eff}$ axis 28 the distance over the upper hemisphere is increased and path 32 is consequently found to terminate at a point 34 which is close to the XY plane. For purposes of illustration, point 34 is shown as being slightly above the XY plane. It is apparent that a further point 36 can be identified, symmetrically disposed with point 34 about the Y axis, from which a second 90°(X) pulse identical to the first pulse will continue to rotate the vector about axis 28 to the $-Z$ pole. A further pulse is now required to produce a transition between points 34, 36 by rotation of the vector with respect to the Y axis. Such a pulse must therefore be phase-shifted by 90° relative to the two 90° pulses. In the presence of offset, rotation in fact occurs about a tilted axis 38 in the ZY plane. If axis 38 intercepts the notional spherical surface of the system at a point 40 and if the offset is considered to be small, then for unit radius the distances from the Y axis to the points 34, 36 and 40 are all equal to $\theta$. For a substantially planar element of the spherical surface the angle subtended at point 40 by points 34, 36 is thus 90°. As a first estimate therefore a pulse of 270°(Y) is required to produce the desired transition from point 34 to point 36, as indicated by an arc 42.

The estimate is oversimplified partly because, for practical values of resonance offset, a planar geometrical representation is no longer adequate and partly because of the increase in the true angle of rotation over the nominal rotation value of the pulse, under the influence of the enhanced field $B_{eff}$. Computer simulation has been used to make a more refined estimate and indicates that a pulse of nominal angle 240°(Y) is preferable. That angle is effective over a practical range of values of resonance offset and is specified in the description of the operation of the spectrometer of FIG. 1 with reference to FIG. 3. It is visualised that for very large offsets the nominal angle of the central pulse of the sequence might be as small as 180°(Y). The initial and final pulses of the sequence have been considered only to be of similar nominal angle 90°(X) and in general it will be convenient to maintain symmetry. It is evident, however, that small variations from 90°(X) could be accommodated by a variation in the rotation angle of the central pulse and it is probable that markedly asymmetric sequences can be found which will be satisfactory.

The condition required for the operation of the invention is therefore only that the elements of the composite pulse have the combined result that inversion is sufficiently complete for effective decoupling.

It has also been found that an alternative form of composite pulse is effective in which two symmetrical pulses are separated by a period of free precession. The trajectory is indicated in FIG. 7. Starting as before from the $+Z$ pole a 270°(X) pulse produces a rotation indicated by a path 48, initially following path 30 (FIG. 5) and continuing round the rear surface of the lower hemisphere. Path 48 terminates at a point 50 near to the XY plane and is displaced by $\theta$ from the $-Y$ axis. A second rotation in a corresponding trajectory 52 which is required to terminate close to the $-Z$ pole must start from the region of a point 54, which is located symmetrically with point 50 about the $-Y$ axis. It is not generally appreciated that following a 270°(X) pulse in the presence of an inclined field $B_{eff}$, a self-corrective precession of the magnetisation will occur from the displaced position 50 towards the $-Y$ axis. A time delay between the pulses can therefore be determined which allows precession to continue until the transition is completed from point 50 to point 54. It can be shown that the delay must be set equal to $2/\gamma B_2$ to allow precession through an angle of approximately $2\theta$ radians where $\theta$ has the value shown in FIG. 4. Provided that $\theta$ is not too large the $2\theta$ relationship remains true whatever the value of the offset $\Delta B$. This alternative composite pulse is more sensitive that the 3-pulse composite to the correct setting of the pulse parameters but has the advantage that r.f. phase shifting of the $B_2$ pulse by 90° is not required so that the spectrometer need not have this facility. The alternative composite pulse (RA) is applied in a sequence corresponding to that illustrated in FIG. 2, i.e. RA1, RA2, $\overline{RA1}$, $\overline{RA2}$ repetitively, so that a 180° phase modulation facility is still needed. The RA sequence provides less effective decoupling than does the R sequence but still shows an improvement over conventional noise decoupling.

Comparative tests have been made between decoupling using a method according to the invention and conventional noise decoupling of 2kHz bandwidth (the best choice of the available bandwidths for the instrument concerned) in determining the sensitivity to resonance offset of the $^{13}C$ spectrum of methyl iodide. Spectra are shown in FIG. 8 for an experiment in which the frequency of the $B_2$ signal is displaced in successive steps of 0.5kHz through a range of 8kHz. The on-resonance condition is at approximately 5kHz. The set of curves 54 is obtained by noise decoupling and the set 56 by means of a method as described above with reference to FIGS. 1 to 3, with the strength of the decoupling field corresponding to 6.3kHz. Normalised peak heights have been calculated which confirm the visual impression of curves 54, 56 that, while the peaks are similar at 5kHz, the peaks of curves 54 fall away quite sharply above and below 5kHz but the peaks of curves 56 are displayed at substantially uniform sensitivity over a much wider band.

A further comparative demonstration of the sensitivity obtained is shown in the spectra of ethyl benzene in FIG. 9. Spectrum 58, obtained with conventional noise decoupling shows considerable narrowing of the broad line groupings which would appear in the presence of coupling. Spectrum 60 shows the same groups decoupled by means of a method as described above with reference to FIGS. 1 to 3. In this case the strength of the decoupling field correspond to 3.1kHz. An improvement in resolution is apparent, but is not readily quantified on the scale of the drawing. An approximate doubling in senstivity is, however, very clearly indicated by the vertical scales in arbitrary units, with some variation in the improvement dependent on the line group structure.

The way in which substantially complete longitudinal inversion is produced by means of a composite pulse has been described and results have been quoted which demonstrate the improved decoupling performance given by a sequence of such pulses as defined by the invention. The theoretical basis for the performance is complex but will be presented in outline, sufficient to demonstrate that spin coupling interactions are substantially completely cancelled when the sequence RRR̄R̄ is followed but that in general cancellation would not be achieved by a perturbation RR̄ or RR alone. Consider the case of weakly coupled spins I and S, where I represents the observed nuclear species (carbon-13) and S the strongly irradiated species (protons). The Hamiltonian for two such weakly coupled spins I and S is expressed as $$H(t) = H_I + H_S(t) \quad (1)$$

where $$H_I = -\Delta\omega_I I_Z + 2\pi J I_Z S_Z, \; H_S(t) = H_{rf}(t) - \Delta\omega_S S_Z$$

In this equation $H_S(t)$ represents a "stirring" of the S spins, made up of a sequence of rotations about tilted effective fields in the rotating frame. The theory can be easily generalised for the case of several coupled I and S spins.

The Liouville operator $L(t)$ for the system described by this Hamiltonian is given in general by $$L(t) = \hat{T} \exp\left[-i \int_0^t H(t')dt'\right] \quad (2)$$

where $\hat{T}$ is the Dyson time-ordering operator. This expression can be shown to be equivalent to $$L(t) = L_S(t) \, \tilde{L}_I(t)$$

where $$L_S(t) = \hat{T} \exp\left[-i \int_0^t H_S(t')dt'\right] \quad (4)$$

$$\tilde{L}_I(t) = \hat{T} \exp\left[-i \int_0^t \tilde{H}_I(t')dt'\right] \quad (5)$$

and $$\tilde{H}_I(t) = L_S^{-1}(t) \, H_I L_S(t) \quad (5)$$

The equations (3)–(5) have the following physical interpretation: $\tilde{H}_I(t)$ represents $H_I$ transformed into a second rotating frame defined by $L_S(t)$. $L_S(t)$ rotates S-spin operators about a sequence of effective fields $B_{eff}(t)$, the resultant of $\Delta B$ and $B_2$. At $t=0$ the second rotating frame is coincident with the conventional rotating frame but rotates about $B_{eff}$ at an angular frequency $\gamma B_{eff}$ radians per second. Since the phase of $B_2$ is switched during the cycle, the rotating frame similarly switches its axis of rotation. Only the part of $H_I$ involving coupling with the S-spins is affected by the transformation. In equation (3) $\tilde{L}_I(t)$ describes the evolution of the system in this second rotating frame, while $L_S(t)$ transforms this back into the conventional reference frame.

Now if a cycle of total duration $\tau$ can be chosen so that the tilted rotations return the S-spin operators to their starting position, then $$L(\tau) = \tilde{L}_{I(\tau)} \, T_m \quad (6)$$

The term $\tilde{L}_I(\tau)$ may be evaluated by average Hamiltonian theory, following the paper by V. Haeberlen and J.S. Waugh, Phys. Rev. 175,453 (1968).

$$\tilde{L}_I(\tau) = \exp[-i\tau(\overline{H}_I^{(0)} + \overline{H}_I^{(1)} + \overline{H}_I^{(2)} + \ldots)] \quad (7)$$

with $$\overline{H}_I^{(0)} = \tau^{-1} \int_0^\tau L_S^{-1}(t) \, H_I L_S(t) dt \quad (8)$$

with

The cycle must be repaid enough to satisfy the condition $2\pi J\tau < 1$, and since the higher-order correction terms $\overline{H}_I^{(n)}$ have magnitudes of the order $(2\pi J\tau)^{n+1} [(n+1)!\tau]$, it is permissible to retain only the zero-order term as a first approximation. Note that it was the choice of the decomposition of the Hamiltonian in Equation (1) which caused the higher-order correction terms to be small; their frequency-dependence is thus unimportant.

The transformed Hamiltonian can be written in general as $$L_S^{-1}(t) \, H_I L_S(t) = -\Delta\omega_I I_Z + 2\pi J I_Z[a(t) \, S_X + b(t) \, S_Y + c(t) S_Z] \quad (9)$$

It is sufficient to calculate the behaviour of the system over the complete cycle to define it for all times. This average is $$\overline{H}_I^{(O)} = -\Delta\omega_I I_Z + 2\pi J I_Z(\overline{a} \, S_X + \overline{b} S_Y + \overline{c} S_Z) \quad (10)$$

Providing that interest lies only in I-spin observables, this can be shown to be equivalent to $$\overline{H}_I^{(O)} = -\Delta\omega_I I_Z + 2 J I_Z S_Z(\overline{a}^2 + \overline{b}^2 + \overline{c}^2)^{\frac{1}{2}} \quad (11)$$

the second term representing the residual IS interaction. This is the term which must vanish if the decoupling is to be effective, and it is clear that each of the averages $\overline{a}\overline{b}$/ and $\overline{c}$ must vanish. The criterion can be satisfied by the sequence of four perturbations RRR̄R̄ provided that R accurately inverts longitudinal magnetisation (R $I_Z R^{-1} = -I_Z$) over the frequency range of interest. The perturbation R̄ is similar except that it employs pulses shifted in phase $\pi$ radians.

$$\overline{R} = R_{-Z}(\pi) R \, R_Z(\pi) \text{ where } R_Z(\pi) = \exp(i\pi I_Z) \quad (12)$$

If each of the four elements of the cycle has a duration $d = \tau/4$, the average Hamiltonian may be written for the first element $$\bar{h}_I^{(0)} = -\Delta\omega_I I_Z + 2\pi J I_Z d^{-1} \int_0^d [a(t)S_X + b(t)S_Y + c(t)S_Z]dt \quad (13)$$

Over the full cycle of length $\tau$:

$$H_I^{(0)} = \tfrac{1}{4}[h_I^{(0)} + R^{-1}\bar{h}_I^{(0)}R + \quad (14)$$

$$R^{-1}R^{-1}R_{-Z(\pi)}\bar{h}_I^{(0)}R_{Z(\pi)}RR +$$

$$R^{-1}R^{-1}(\bar{R})^{-1}R_{-Z(\pi)}\bar{h}_I^{(0)}R_{Z(\pi)}\bar{R}RR]$$

Using the property $R^2 = 1$, it can be shown that the combination of the first term with the third, and the second with the fourth, cancels the mean values $\bar{a}$ and $\bar{b}$, while the combinations of the first with the second, and third with the fourth, cancels $\bar{c}$. Thus $$H_I^{(O)} = -\Delta\omega_I I_Z \quad (15)$$

which is the decoupled I-spin Hamiltonian.

I claim:

1. A method of heteronuclear decoupling in high resolution pulsed NMR spectroscopy, in which during the acquisition from a sample of signals resulting from resonance of a nuclear species to be observed the sample is irradiated with radio frequency energy substantially at the resonant frequency of an interfering nuclear species, the irradiation being in the form of a train of composite pulses each of which is effective to cause at least approximate inversion of the longitudinal magnetisation in respect of said interfering nuclear species, said composite pulses being of two types which differ only by virtue of the r.f. phase for one type being opposite that for the other type and said train being in the form of a repeated sequence which consists of two pulses of each type and which involves less than three changes of type between successive pulses.

2. A method according to claim 1, 5 or 6 in which each of said composite pulses consists of three constituent pulses with negligible intervals between them, the first and third constituent pulses having the same r.f. phase and each being of nominal duration $\pi/2\gamma B_2$, and the second constituent pulse having a r.f. phase which differs by 90° from that of the first and third constituent pulses and having a nominal duration between $\pi/\gamma B_2$ and $3\pi/2\gamma B_2$, where $B_2$ is the magnetic flux density associated with the r.f. irradiation and $\gamma$ is the gyromagnetic ratio for said interfering nuclear species.

3. A method according to claim 2, in which the nominal duration of said second constituent pulse is $4\pi/3\gamma B_2$.

4. A method according to claim 1, 5 or 6 in which each of said composite pulses consists of two constituent pulses having the same r.f. phase and each of nominal duration $3\pi/2\gamma B_2$, said constituent pulses being separated by an interim period of duration approximately $2/\gamma B_2$, where $B_2$ is the magnetic flux density associated with the r.f. irradiation and $\gamma$ is the gyromagnetic ratio for said interfering nuclear species.

5. A method of heteronuclear decoupling in high resolution pulsed NMR spectroscopy, in which:
during the acquisition from a sample of signals resulting from resonance of a nuclear species to be observed, the sample is irradiated with radio frequency energy substantially at the resonant frequency of an interfering nuclear species,
the irradiation being in the form of a train of composite pulses each of which is effective to cause at least approximate inversion of the longitudinal magnetisation in respect of said interfering nuclear species,
said composite pulses being of two types which differ only by virtue of the r.f. phase for one type being opposite that for the other type and said train being in the form of a repeated sequence having equal numbers of the pulses of each type with the number of each type being at least two.

6. A method of heteronuclear decoupling in high resolution pulsed NMR spectroscopy, in which:
during the acquisition from a sample of signals resulting from resonance of a nuclear species to be observed, the sample is irradiated with radio frequency energy substantially at the resonant frequency of an interfering nuclear species,
the irradiation being in the form of a train of composite pulses each of which is effective to cause at least approximate inversion of the longitudinal magnetisation in respect of said interfering nuclear species,
said composite pulses being of two types which differ only by virtue of the r.f. phase for one type of being opposite that for the other type and said train being in the form of a repeated sequence which includes $2^N$ pulses of each type, where N is a positive integer.

* * * * *

UNITED STATES PATENT AND TRADEMARK OFFICE
CERTIFICATE OF CORRECTION

PATENT NO. : 4,443,761
DATED : April 17, 1984
INVENTOR(S) : Malcolm H. LEVITT

It is certified that error appears in the above-identified patent and that said Letters Patent is hereby corrected as shown below:

On the Title Page:

Item [30] Foreign Application Priority Data read "June 16, 1981" as --June 19, 1981--

Signed and Sealed this

Twenty-sixth Day of March 1985

[SEAL]

*Attest:*

DONALD J. QUIGG

*Attesting Officer*      *Acting Commissioner of Patents and Trademarks*